US010239023B2

(12) United States Patent
Stasiak et al.

(10) Patent No.: US 10,239,023 B2
(45) Date of Patent: *Mar. 26, 2019

(54) SELF-WETTING POROUS MEMBRANES (II)

(71) Applicant: PALL CORPORATION, Port Washington, NY (US)

(72) Inventors: Marcin Stasiak, Port Washington, NY (US); Hassan Ait-Haddou, Melville, NY (US)

(73) Assignee: Pall Corporation, Port Washington, NY (US)

( * ) Notice: Subject to any disclaimer, the term of this patent is extended or adjusted under 35 U.S.C. 154(b) by 20 days.

This patent is subject to a terminal disclaimer.

(21) Appl. No.: 14/750,443

(22) Filed: Jun. 25, 2015

(65) Prior Publication Data

US 2016/0375412 A1 Dec. 29, 2016

(51) Int. Cl.
*B01D 71/68* (2006.01)
*B01D 67/00* (2006.01)
(Continued)

(52) U.S. Cl.
CPC .............. *B01D 71/68* (2013.01); *A61M 1/16* (2013.01); *B01D 67/002* (2013.01);
(Continued)

(58) Field of Classification Search
CPC ...... B01D 71/06; B01D 71/68; B01D 67/002; B01D 71/28; B01D 71/80; B01D 67/0016;
(Continued)

(56) References Cited

U.S. PATENT DOCUMENTS 3,318,959 A 5/1967 Borman
3,847,867 A 11/1974 Heath et al.
(Continued)

FOREIGN PATENT DOCUMENTS

CN 102755844 A 10/2012
CN 104703681 A 6/2015
(Continued)

OTHER PUBLICATIONS

European Patent Office, Extended European Search Report issued in European Patent Application No. 16167504.6 (dated Oct. 28, 2016) 8 pp.
(Continued)

*Primary Examiner* — Taiwo Oladapo
(74) *Attorney, Agent, or Firm* — Leydig, Voit & Mayer, Ltd.

(57) ABSTRACT

Disclosed is a self-wetting porous membrane comprising an aromatic hydrophobic polymer such as polysulfone and a wetting agent comprising a copolymer of formula A-B or A-B-A, wherein A is a hydrophilic segment comprising a polymerized monomer of the formula (I): $CH_2=C(R^1)(R^2)$, wherein $R^1$ and $R^2$ are as described herein, and B is polyethersulfone, wherein segments B and A are linked through an oxygen atom. Also disclosed is a method of preparing a self-wetting membrane comprising casting a solution containing an aromatic hydrophobic polymer and the wetting agent, followed by subjecting the cast solution to phase inversion. The self-wetting porous membrane finds use in hemodialysis, microfiltration, and ultrafiltration.

17 Claims, 2 Drawing Sheets

US 10,239,023 B2

Page 2

(51) Int. Cl.
<table>
<tr><td>B01D 71/80</td><td>(2006.01)</td></tr>
<tr><td>A61M 1/16</td><td>(2006.01)</td></tr>
<tr><td>B01D 71/28</td><td>(2006.01)</td></tr>
<tr><td>B29C 39/02</td><td>(2006.01)</td></tr>
<tr><td>B29C 44/02</td><td>(2006.01)</td></tr>
<tr><td>C02F 1/44</td><td>(2006.01)</td></tr>
<tr><td>B29K 81/00</td><td>(2006.01)</td></tr>
<tr><td>B29L 31/14</td><td>(2006.01)</td></tr>
</table>

(52) U.S. Cl.
CPC ......... *B01D 67/0016* (2013.01); *B01D 71/28* (2013.01); *B01D 71/80* (2013.01); *B29C 39/02* (2013.01); *B29C 44/02* (2013.01); *C02F 1/44* (2013.01); *B01D 2325/36* (2013.01); *B29K 2081/06* (2013.01); *B29L 2031/14* (2013.01)

(58) Field of Classification Search
CPC ..... B01D 2325/36; B29C 44/02; B29C 39/02; A61M 1/16; C02F 1/44; B29K 2081/06; B29L 2031/14
See application file for complete search history.

(56) References Cited

U.S. PATENT DOCUMENTS

<table>
<tr><td>4,611,048 A</td><td>9/1986</td><td>Peters</td><td></td></tr>
<tr><td>5,885,456 A</td><td>3/1999</td><td>Charkoudian et al.</td><td></td></tr>
<tr><td>5,911,880 A</td><td>6/1999</td><td>Klein et al.</td><td></td></tr>
<tr><td>6,113,785 A</td><td>9/2000</td><td>Miura et al.</td><td></td></tr>
<tr><td>7,230,066 B2</td><td>6/2007</td><td>Khouri et al.</td><td></td></tr>
<tr><td>2003/0055179 A1</td><td>3/2003</td><td>Ota et al.</td><td></td></tr>
<tr><td>2011/0240550 A1*</td><td>10/2011</td><td>Moore ...............</td><td>B01D 67/0011<br>210/490</td></tr>
<tr><td>2012/0111791 A1*</td><td>5/2012</td><td>Freeman ................</td><td>B01D 65/08<br>210/500.34</td></tr>
<tr><td>2015/0151256 A1</td><td>6/2015</td><td>Abetz et al.</td><td></td></tr>
</table>

FOREIGN PATENT DOCUMENTS

<table>
<tr><td>EP</td><td>0318787 A2</td><td>6/1989</td></tr>
<tr><td>JP</td><td>S62-201603 A</td><td>9/1987</td></tr>
<tr><td>JP</td><td>H02-160026 A</td><td>6/1990</td></tr>
<tr><td>JP</td><td>H09-122462 A</td><td>5/1997</td></tr>
<tr><td>JP</td><td>2001-310917 A</td><td>11/2001</td></tr>
<tr><td>JP</td><td>4000196 B1</td><td>10/2007</td></tr>
<tr><td>JP</td><td>2015-529555 A</td><td>10/2015</td></tr>
<tr><td>JP</td><td>2015-529555 T</td><td>10/2015</td></tr>
<tr><td>WO</td><td>WO 97/013575 A1</td><td>4/1997</td></tr>
<tr><td>WO</td><td>WO 2011/123033 A1</td><td>10/2011</td></tr>
<tr><td>WO</td><td>WO 2014/181931 A1</td><td>11/2014</td></tr>
<tr><td>WO</td><td>WO 2015/075178 A1</td><td>5/2015</td></tr>
</table>

OTHER PUBLICATIONS

Taiwanese Intellectual Property Office, Examination Report issued in Taiwanese Patent Application No. 105112790 (dated Jan. 10, 2017).

U.S. Appl. No. 14/750,382, filed Jun. 25, 2015.

Asif, A., et al., "Hydroxyl Terminated Poly(ether ether ketone) with Pendant Methyl Group-Toughened Epoxy Clay Ternary Nanocomposites: Preparation, Morphology, and Thermomechanical Properties," *Journal of Applied Polymer Science*, vol. 106, pp. 2936-2946 (2007).

Dizman, Cemil, et al., "Synthesis of polysulfone-b-polystyrene block copolymers by mechanistic transformation from condensation polymerization to free radical polymerization," *Polymer Bulletin*, vol. 70, pp. 2097-2109 (2013).

Francis, Bejoy, et al., "Synthesis of Hydroxyl-Terminated Poly(ether ether ketone) with Pendent tert-Butyl Groups and Its Use as a Toughener for Epoxy Resins," *Journal of Polymer Science: Part B: Polymer Physics*, vol. 44, pp. 541-556 (2006).

Riffle, J.S., et al., "Synthesis of Hydroxyl-Terminated Polycarbonates of Controlled Number-Average Molecular Weight," *Journal of Polymer Science: Polymer Chemistry Edition*, vol. 20, pp. 2289-2301 (1982).

Wang, Jianyu, et al., "Amphiphilic ABA copolymers used for surface modification of polysulfone membranes, Part 1: Molecular design, synthesis, and characterization," *Polymer*, vol. 49, pp. 3256-3264 (2008).

Yang, Jung-Eun, et al., "Synthesis and Morphology Studies of a Polystyrene-Poly(arylene ether sulfone)-Polystyrene Coil-Semirod-Coll Triblock Copolymer," *Macromolecules*, vol. 39, pp. 3038-3042 (2006).

Yi, Zhuan, et al., "An extending of candidate for the hydrophilic modification of polysulfone membranes from the compatibility consideration: The polyethersulfone-based amphiphilic copolymer as an example," *Journal of Membrane Science*, vol. 390-391, pp. 48-57 (2012).

Yi, Zhuan, et al., "Effects of coagulant pH and ion strength on the dehydration and self-assembly of poly(N, N-dimethylamino-2-ethyl methacrylate) chains in the preparation of stimuli-responsive polyethersulfone blend membranes," *Journal of Membrane Science*, vol. 463, pp. 49-57 (2014).

Zhang, Ping, et al., "Structure and Properties of Poly(butyl acrylate-block-sulfone-block-butyl acrylate) Triblock Copolymers Prepared by ATRP," *Macromolecular Chemistry and Physics*, vol. 206, pp. 33-42 (2005).

Zhao, Yi-Fan, et al., "Versatile antifouling polyethersulfone filtration membranes modified via surface grafting of zwitterionic polymers from a reactive amphiphilic copolymer additive," *Journal of Colloid and Interface Science*, vol. 448, pp. 380-388 (2015).

Zhao, Yi-Fan, et al., "Improving the hydrophilicity and fouling-resistance of polysulfone ultrafiltration membranes via surface zwitterionicalization mediated by polysulfone-based triblock copolymer additive," *Journal of Membrane Science*, vol. 440, pp. 40-47 (2013).

Zhao, Yi-Fan, et al.,"Zwitterionic hydrogel thin films as antifouling surface layers of polyethersulfone ultrafiltration membranes anchored via reactive copolymer additive," *Journal of Membrane Science*, vol. 470, pp. 148-158 (2014).

Intellectual Property Office of Singapore, Search Report issued in Singapore Patent Application No. 10201603254S (dated Jul. 25, 2016).

Barton et al., "The effect of phenols and aromatic thiols on the polymerization of methyl methacrylate", *Canadian Journal of Chemistry*, vol. 41, No. 11, pp. 2737-2742 (1963).

Japanese Patent Office, Notice of Reasons for Rejection issued in Japanese Patent Application No. 2016-088422 (dated May 23, 2017) 6 pp.

Taiwan Intellectual Property Office, Examination and Search Report issued in Japanese Patent Application No. 105112790 (dated Apr. 27, 2017) 11 pp.

Korean Intellectual Property Office, Notice of Non-Final Rejection issued in Korean Patent Application No. 10-2016-0052068 (dated Apr. 19, 2017).

Taiwan Intellectual Property Office, Rejection Decision issued in Taiwanese Application No. 105112790 (dated Oct. 19, 2017).

Korean Intellectual Property Office, Notice of Non-Final Rejection issued in Korean Application No. 10-2016-0052068 (dated Oct. 30, 2017).

Japan Patent Office, Notice of Reasons for Rejection issued in Japanese Application No. 2016-088422 (dated Dec. 5, 2017).

Taiwan Intellectual Property Office, Examination and Search Report issued in Taiwanese Patent Application No. 105112790 (dated Apr. 27, 2017) 11 pp.

European Patent Office, Communication pursuant to Article 94(3) EPC, issued in European Patent Application No. 16167504.6 (dated Apr. 11, 2018) 5 pp.

State Intellectual Property Office of the People's Republic of China, Office Action issued in Chinese Patent Application No. 201610490968.6 (dated Aug. 23, 2018) 24 pp.

Taiwan Intellectual Property Office, Examination Report issued in Taiwanese Patent Application No. 105112790 (dated May 7, 2018) 3 pp.

(56) References Cited

OTHER PUBLICATIONS

Korean Intellectual Property Office, Examination Report issued in Korean Patent Application No. 10-2016-0052068 (dated May 30, 2018) 8 pp.
Korean Intellectual Property Office, Reexamination Report issued in Korean Patent Application No. 10-2016-0052068 (dated Jul. 5, 2018) 23 pp.
State Intellectual Property Office of the People's Republic of China, Office Action issued in Chinese Patent Application No. 201610490968.6 (dated Jan. 23, 2019) 24 pp.
Zhao et al., "Enhancing the Antifouling and Antimicrobial Properties of Poly(ether sulfone) Membranes by Surface Quaternization from a Reactive Poly(ether sulfone) Based Copolymer Additive," *Industrial & Engineering Chemistry Research*, 53: 13952-13962 (2014).

* cited by examiner

SELF-WETTING POROUS MEMBRANES (II)

BACKGROUND OF THE INVENTION

Aromatic hydrophobic polymers such as polysulfone and polyethersulfone are attractive as membrane polymers for one or more of the following reasons: a high glass transition temperatures, amorphous glassy state, thermal and oxidative stability, excellent strength and flexibility, resistance to extreme pHs, and low creep even at elevated temperatures. However, these polymers are inherently hydrophobic and therefore porous membranes made from these polymers are not wettable by water.

Attempts have been made to improve the surface wettability of porous membranes made from such polymers by numerous methods including coating and crosslinking a hydrophilic polymer, grafting of hydrophilic monomers by e-beam, gamma radiation, or UV or other radiation, surface oxidation, surface-initiated free radical grafting, blending with hydrophilic additives such as polyvinylpyrrolidone (PVP), copolymers of PVP, polyvinylalcohol (PVA), copolymers of PVA, polyethylene oxide (PEO), copolymers of PEO and polypropylene oxide, and in situ polymerization of hydrophilic monomers.

Drawbacks are associated with one or more of the above attempted methods. For example, with the methods involving blending of hydrophilic additives, the additives tend to leach out of the porous membrane on prolonged use in aqueous environments. Approaches involving coating and crosslinking a hydrophilic polymer tend to shrink or modify the membrane pores, thereby limiting the usefulness of the membranes.

The foregoing shows that there exists an unmet need for preparing porous membranes from aromatic hydrophobic polymers that would produce water wettable surfaces and the surface wettability would be stable over extended periods of use.

BRIEF SUMMARY OF THE INVENTION

The invention provides a self-wetting porous membrane comprising an aromatic hydrophobic polymer and a wetting agent comprising a copolymer of formula A-B or A-B-A, wherein A is a hydrophilic segment comprising a polymerized monomer or mixture of monomers, wherein the monomer is of the formula (I):

$$CH_2=C(R^1)(R^2) \qquad (I),$$

wherein $R^1$ is hydrogen or alkyl, and $R^2$ is selected from substituted or unsubstituted heterocyclyl, substituted or unsubstituted heteroaryl, formylamino, formylaminoalkyl, aminocarbonyl, alkylcarbonyloxy, and aminocarbonylalkyl substituted with a zwitterionic group, and B is polyethersulfone, wherein segments B and A are linked through an oxygen atom. The invention also provides a method of preparing such a self-wetting porous membrane.

The self-wetting porous membrane of the invention has high water wettability as evidenced by its high critical wetting surface tension (CWST) of 71 dynes/cm$^2$. The wetting additive has high degree of compatibility with the aromatic hydrophobic polymer and therefore does not leach out or leaches out only minimally. The wetting additive also distributes itself uniformly in the porous membrane. The porous membrane has high water permeability, for example, in the range of 330-620 LMH. The porous membrane also has a low non-specific protein binding (BSA), indicated by low level of fouling.

BRIEF DESCRIPTION OF THE SEVERAL VIEWS OF THE DRAWING(S)

DETAILED DESCRIPTION OF THE INVENTION

Figure 1:
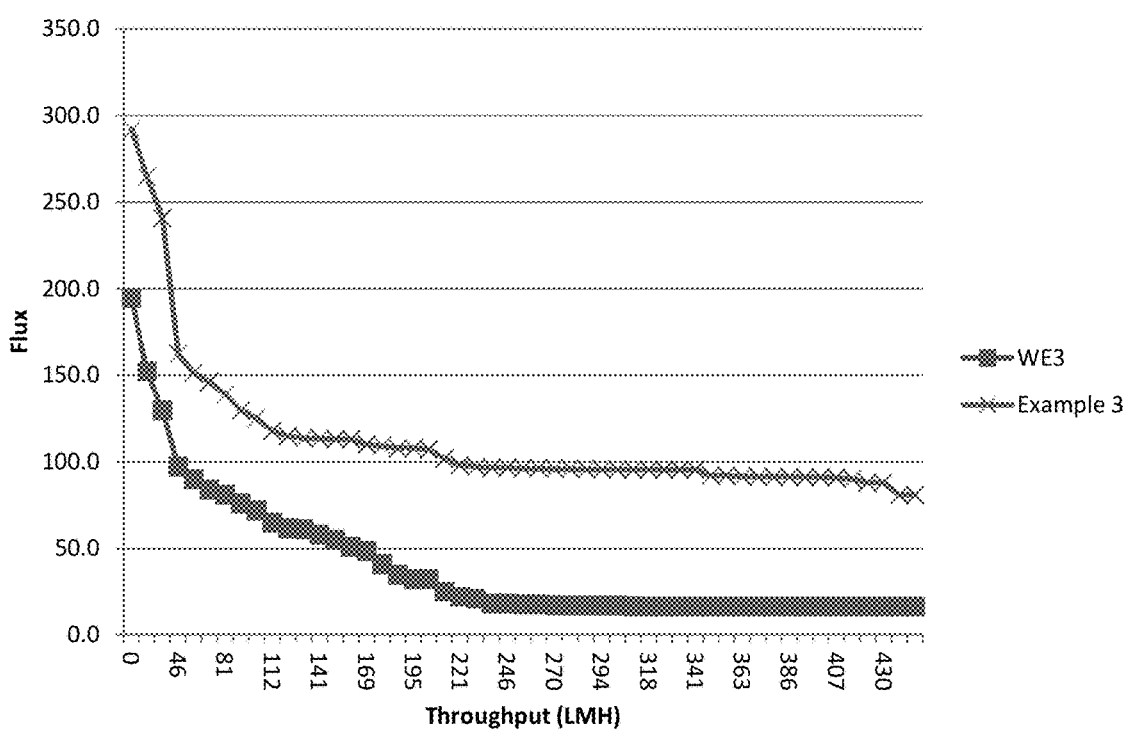
FIG. 1 depicts the BSA flux as a function of throughput for a PES membrane prepared with a WE3 wetting agent (PVP-co-PVAc) and a self-wetting membrane prepared with copolymer of Example 3 having 51 mol % of PVP in accordance with an embodiment of the invention.

In an embodiment, the invention provides a self-wetting porous membrane comprising an aromatic hydrophobic polymer and a wetting agent comprising a copolymer of formula A-B or A-B-A, wherein A is a hydrophilic segment comprising a polymerized monomer or mixture of monomers, wherein the monomer is of the formula (I):

$$CH_2=C(R^1)(R^2) \qquad (I),$$

wherein $R^1$ is hydrogen or alkyl, and $R^2$ is selected from substituted or unsubstituted heterocyclyl, substituted or unsubstituted heteroaryl, formylamino, formylaminoalkyl, aminocarbonyl, alkylcarbonyloxy, and aminocarbonylalkyl substituted with a zwitterionic group, and B is polyethersulfone, wherein segments B and A are linked through an oxygen atom. "A" further comprises an end group.

The term "heterocyclyl" as used herein refers to a monocyclic heterocyclic group or a bicyclic heterocyclic group. The monocyclic heterocycle is a three-, four-, five-, six- or seven-membered ring containing at least one heteroatom independently selected from the group consisting of O, N, N(H) and S. The three- or four-membered ring contains zero or one double bond and a heteroatom selected from the group consisting of O, N, N(H) and S. The five-membered ring contains zero or one double bond, and one, two or three heteroatoms selected from the group consisting of O, N, N(H) and S. The six-membered ring contains zero, one or two double bonds and one, two or three heteroatoms selected from the group consisting of O, N, N(H) and S. The seven-membered ring contains zero, one, two, or three double bonds and one, two or three heteroatoms selected from the group consisting of O, N, N(H) and S. The monocyclic heterocycle can be unsubstituted or substituted and is connected to the parent molecular moiety through any substitutable carbon atom or any substitutable nitrogen atom contained within the monocyclic heterocycle.

Examples of heterocyclyl groups include pyridyl, piperidinyl, piperazinyl, pyrazinyl, pyrolyl, pyranyl, tetrahydropyranyl, tetrahydrothiopyranyl, pyrrolidinyl, pyrrolidinonyl, furanyl, tetrahydrofuranyl, thiophenyl, tetrahydrothiophenyl, purinyl, pyrimidinyl, thiazolyl, thiazolidinyl, thiazolinyl, oxazolyl, triazolyl, tetrazolyl, tetrazinyl, benzoxazolyl, morpholinyl, thiophorpholinyl, quinolinyl, and isoquinolinyl.

The term "heteroaryl" refers to a cyclic aromatic radical having from five to ten ring atoms of which at least one atom is O, S, or N, and the remaining atoms are carbon. Examples of heteroaryl radicals include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl.

Substituents on the heterocyclyl or the heteroaryl moiety can be alkyl, halo, hydroxy, nitro, carboxy, keto, oxo, amino, sulfoxy, sulfonyl, sulfonyloxy, phospho, phosphono, or any combination thereof. For example, a ring $CH_2$ group can be replaced by a C=O group. Substitution can be on a carbon atom or on a hetero atom such as ring nitrogen, for example, an alkyl group on ring nitrogen providing a quaternary ammonium group.

In accordance with an embodiment, the alkyl group is preferably a $C_1$-$C_6$ alkyl. Examples of alkyl groups include methyl, ethyl, n-propyl, isopropyl, n-butyl, sec-butyl, isobutyl, tert-butyl, n-pentyl, isopentyl, n-hexyl, and the like.

A zwitterionic group comprises a positively charged group and a negatively charged group separated by a suitable spacer atom, such as carbon, oxygen, or sulfur, or a moiety such as an alkyl moiety. Examples of positively charged groups include ammonium and quaternary ammonium groups. Examples negatively charged groups include carboxylate, sulfonate, and phosphonate.

In an embodiment, $R^1$ is hydrogen or methyl, and $R^2$ is selected from pyrrolidinonyl, pyridinyl, imidazolyl, N-methylimidazolyl, formylamino, formylaminomethyl, aminocarbonyl, methylcarbonyloxy, and aminocarbonylpropyl substituted with a zwitterionic group.

In a particular embodiment, A is a hydrophilic segment comprising a polymerized monomer or mixture of monomers selected from 1-vinylpyrrolid-2-one, N-[3-(dimethylamino)propyl]methacrylamide, vinyl acetate, 1-vinylimidazole, 1-vinyl-3-alkylimidazolinium, 1-vinyl-2-pyridine, 1-vinyl-4-pyridine, acrylamide, N-vinylformamide, and N-allylformamide, and 3-(methacrylamidopropyl)dimethyl (3-sulfopropyl)ammonium inner salt.

The aromatic hydrophobic polymer to form the membrane can be selected from polysulfone (PSU), polyphenylene ether sulfone (PPES), polyethersulfone (PES), polycarbonate (PC), polyether ether ketone (PEEK), poly(phthalazinone ether sulfone ketone) (PPESK), polyphenyl sulfide (PPS), polyphenyl ether (PPE), polyphenylene oxide (PPO) and polyetherimide (PEI), which have the following structures:

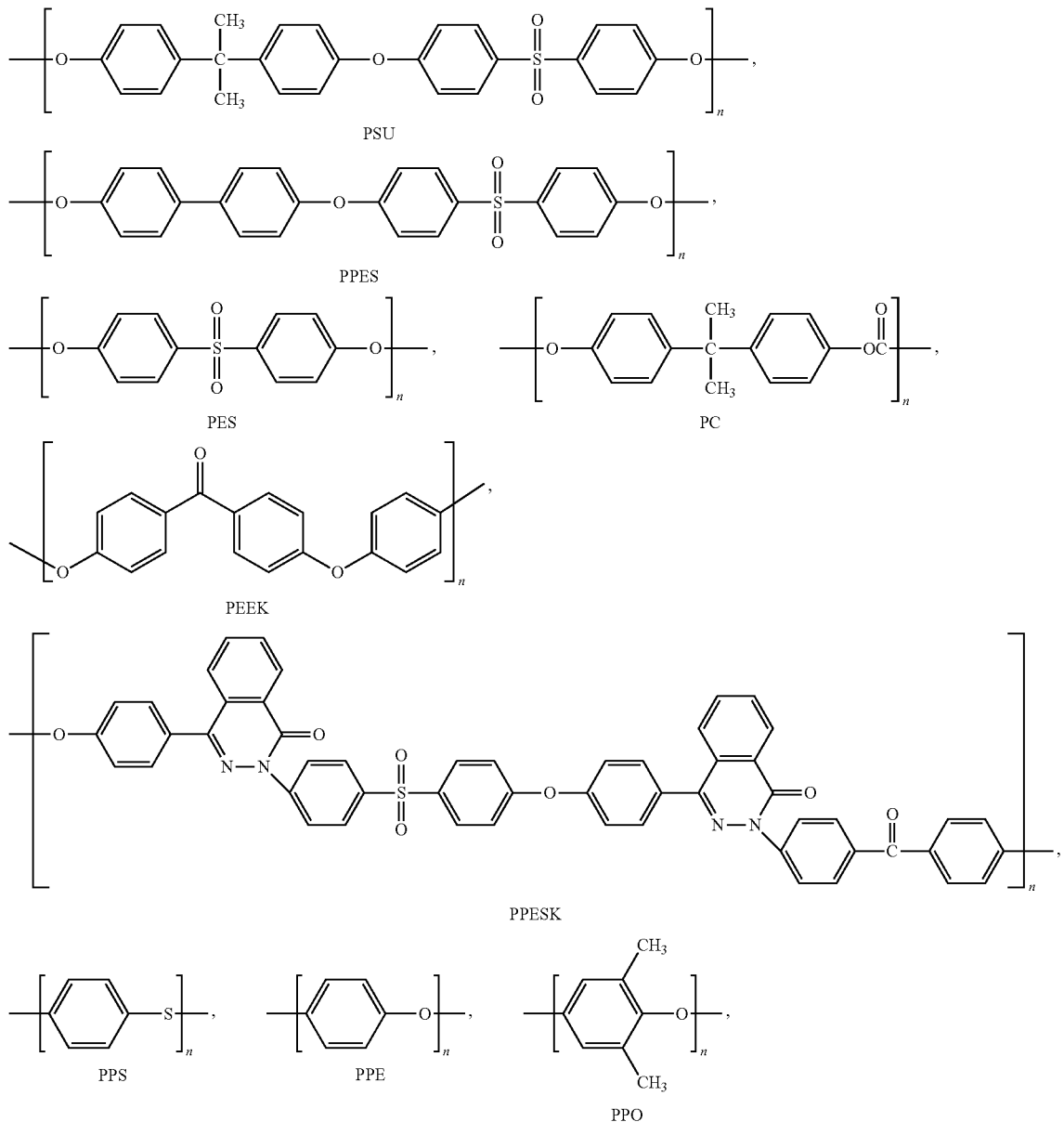

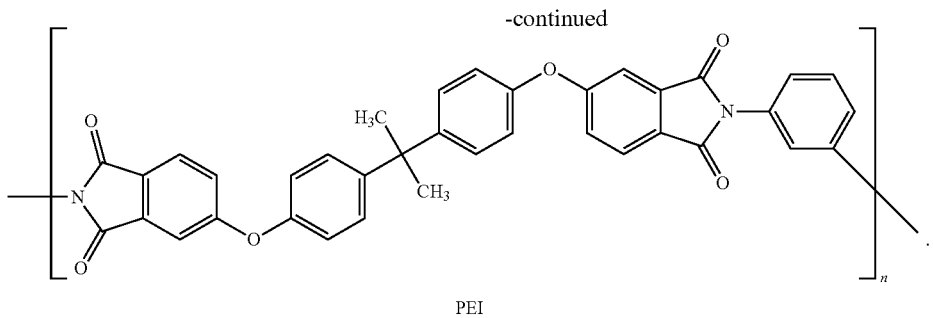
PEI

The aromatic hydrophobic polymer can have any suitable molecular weight, for example, a number average molecular weight of from about 25 kDa to about 250 kDa, preferably from about 50 kDa to about 100 kDa. The value of "n" in the aromatic hydrophobic polymer can be from about 30 to about 300, preferably from about 50 to about 250.

The aromatic hydrophobic polymeric segment B of the copolymer is polyethersulfone terminated with one or preferably two phenolic moieties. Such phenol-substituted moiety can be introduced by carrying out polycondensation in presence of excess of bisphenol S versus the bis(4-chlorophenyl)sulfone (or its fluoro-analog), as is known to those skilled in the art.

The number of repeat units, n, within each of the above aromatic hydrophobic segment B can be from about 10 to about 250, preferably from about 20 to about 200, and more preferably from about 30 to about 100.

The number average molecular weight of the block copolymer is in the range of from about 5,000 to about 50,000 grams/mole, preferably about 10,000 to about 40,000 grams/mole.

In accordance with an embodiment, the copolymer is of the formula (Ia) or (Ib):

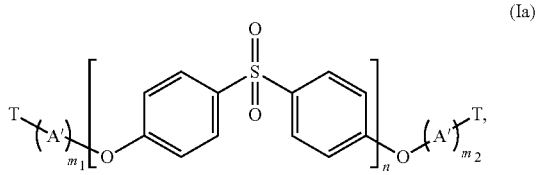
(Ia)

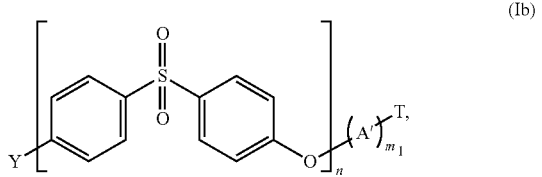
(Ib)

wherein A' is a polymeric segment of the hydrophilic monomer, T is an end group, and Y is chloro or fluoro.

Specific examples of the copolymer include:

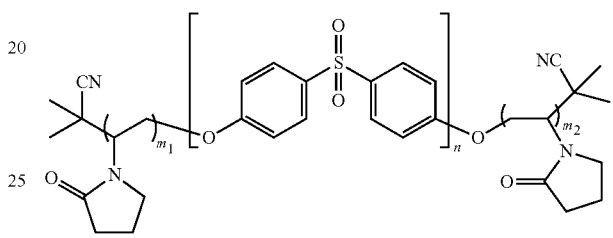

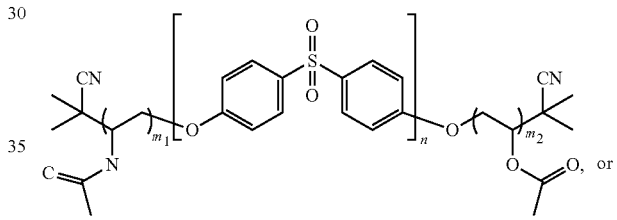
, or

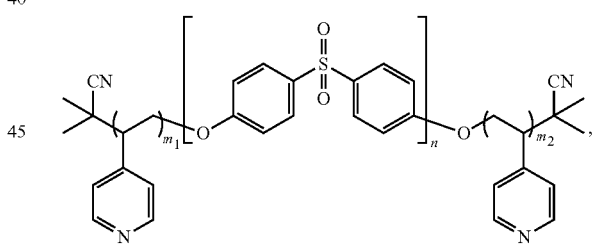
, wherein $m_1$ or $m_2$ is from about 5 to about 80 and preferably from about 20 to about 60, and n is from about 20 to about 200 and preferably from about 30 to about 100.

Diblock copolymers of the type A-B can be prepared from a polymeric segment B having one terminal hydroxyl group and triblock copolymers of the A-B-A can be prepared from a polymeric segment B having two terminal hydroxyl groups.

For example, the 1-vinylpyrrolid-2-one monomer can be polymerized on a preformed polymeric segment B. An example of a polymeric segment B that is commercially available is Solvay's bis-telechelic polyethersulfone VW-10700RP which has hydroxyl end groups. 1-Vinylpyrrolid-2-one is polymerized on the polymer as illustrated below:

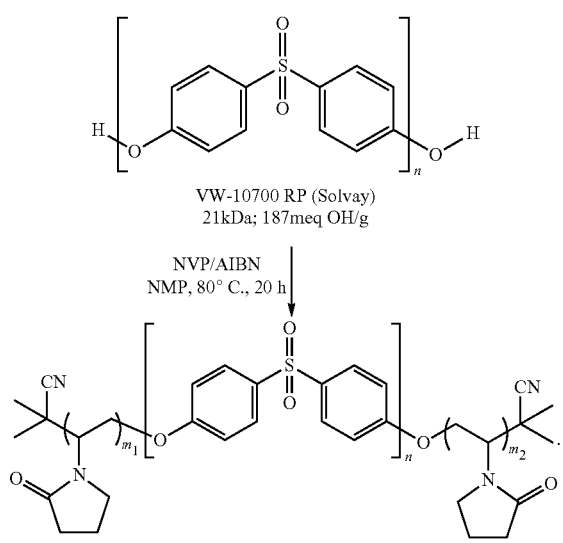

Any suitable free radical initiator can be employed, for example, azoisobutyronitrile (AIBN), benzoyl peroxide, acetyl peroxide, lauryl peroxide, t-butyl peroxide, cumyl peroxide, t-butylperacetate, and t-butyl hydroperoxide.

Accordingly, the nature of the copolymers' end group (T in formulas (Ia) and (Ib)) can vary depending on the initiator employed. The 2-methylpropionitrile end group present in the formulas of the present invention is derived from the termination of the copolymerization with the radical generated from AIBN. Examples of other the end groups are benzoate, acetate, laurate, t-butyloxy, cumyloxy, and the like.

The present invention further provides a method of preparing a self-wetting porous membrane comprising: (i) casting a solution comprising a solvent, an aromatic hydrophobic polymer, and a copolymer of formula A-B-A, wherein A is a hydrophilic segment comprising a polymerized monomer or mixture of monomers, wherein the monomer is of the formula (I):

$$CH_2=C(R^1)(R^2) \qquad (I),$$

wherein $R^1$ is hydrogen or alkyl, and $R^2$ is selected from substituted or unsubstituted heterocyclyl, substituted or unsubstituted heteroaryl, formylamino, formylaminoalkyl, aminocarbonyl, alkylcarbonyloxy, and aminocarbonylalkyl substituted with a zwitterionic group, and B is polyethersulfone, wherein segments B and A are linked through an oxygen atom, to a desired shape; (ii) subjecting the cast solution to phase inversion to form the self-wetting porous membrane; and (iii) optionally rinsing the self-wetting porous membrane with water.

The present invention further provides a self-wetting porous membrane prepared by the method described above.

In accordance with an embodiment of the invention, the self-wetting porous membrane is a porous membrane, e.g., a nanoporous membrane, for example, a membrane having pores of diameter between 1 nm and 100 nm, or a microporous membrane having pores of diameter between 1 μm and 10 μm.

A membrane-forming polymer solution is prepared by dissolving the polymer in a solvent or a mixture of solvents. A variety of polymers are suitable for use as membrane-forming polymers in the invention, and are known in the art. Suitable polymers can include, polymers such as, for example, polysulfone (PSU), polyethersulfone (PES), poly-phenyl ether (PPE), polyphenylene ether sulfone (PPES), polyphenylene oxide (PPO), polycarbonate (PC), poly (phthalazinone ether sulfone ketone) (PPESK), polyether ether ketone (PEEK), polyether ketone ketone (PEKK) and polyetherimide (PEI) and blends thereof.

In addition to one or more polymers, typical polymer solutions comprise at least one solvent, and may further comprise at least one non-solvent. Suitable solvents include, for example, N,N-dimethylformamide (DMF); N,N-dimethyl acetamide (DMAC); N-methylpyrrolidone (NMP); dimethyl sulfoxide (DMSO), methyl sulfoxide, and mixtures thereof. Suitable nonsolvents include, for example, water; various polyethylene glycols (PEGs; e.g., PEG-200, PEG-300, PEG-400, PEG-1000); various polypropylene glycols; various alcohols, e.g., methanol, ethanol, isopropyl alcohol (IPA), amyl alcohols, hexanols, heptanols, and octanols.

Typically, the copolymer A-B-A of the present invention is included in an amount of from about 3 to about 20 wt. %, preferably in the range of about 4 to about 15 wt. % in the membrane casting solution.

The membrane casting solution typically includes about 10 to about 30 wt. % of the aromatic hydrophobic polymer, about 0 to about 10 wt % an additive such as PEG, a polar solvent or mixture of solvents such as NMP, DMF, and/or DMAc in an amount up to about 90 wt %. A nonsolvent such as water and/or alcohol can also be included.

Typical quenching baths that may be utilized in the formation of the self-wetting membranes include, but are not limited to, baths which contain non-solvents such as water, alcohols and the like, either by themselves, or in combination with one or more polar solvents.

Suitable components of solutions are known in the art. Illustrative solutions comprising polymers, and illustrative solvents and nonsolvents include those disclosed in, for example, U.S. Pat. Nos. 4,340,579; 4,629,563; 4,900,449; 4,964,990, 5,444,097; 5,846,422; 5,906,742; 5,928,774; 6,045,899; 6,146,747; and 7,208,200.

The aromatic hydrophobic polymer, the copolymer, and the solvent and other additives are first mixed together and then heated at a temperature of about 55 to about 75° C., preferably about 60 to about 65° C., until a homogeneous solution is obtained.

Flat sheet membranes can be prepared on a suitable substrate such as glass by casting a film having a suitable thickness, e.g., about 0.005 to about 0.006 inch using a doctoring knife. The cast film is coagulated in a quenching bath and washed in water for a period of time which is sufficient to leach out any material that is not directly bound to the hydrophobic-base polymer. The membrane is dried by methods known to those skilled in the art.

In addition to preparing flat sheet membranes, the self-wetting membranes of the instant invention can be formed into pleated membranes, hollow fiber membranes, tubular membranes and the like using processes that are well known in the art.

The present invention further provides a method of filtering a fluid, the method comprising passing the fluid through the self-wetting porous membrane.

Self-wetting porous membranes according to embodiments of the invention can be used in a variety of applications, including, for example, hemodialysis, microfiltration, and ultrafiltration applications. Additionally they may also find use in diagnostic applications (including, for example, sample preparation and/or diagnostic lateral flow devices), ink jet applications, lithography, e.g., as replacement for HD/UHMW PE based media, filtering fluids for the pharmaceutical industry, metal removal, production of ultrapure water, treatment of industrial and surface waters, filtering fluids for medical applications (including for home and/or for patient use, e.g., intravenous applications, also including, for example, filtering biological fluids such as blood (e.g., virus removal)), filtering fluids for the electronics industry, filtering fluids for the food and beverage industry, beer filtration, clarification, filtering antibody- and/or protein-containing fluids, filtering nucleic acid-containing fluids, cell detection (including in situ), cell harvesting, and/or filtering cell culture fluids. Alternatively, or additionally, porous membranes according to embodiments of the invention can be used to filter air and/or gas and/or can be used for venting applications (e.g., allowing air and/or gas, but not liquid, to pass therethrough). Porous membranes according to embodiments of the invention can be used in a variety of devices, including surgical devices and products, such as, for example, ophthalmic surgical products.

In accordance with embodiments of the invention, the self-wetting porous membrane can have a variety of configurations, including planar, flat sheet, pleated, tubular, spiral, and hollow fiber.

Self-wetting porous membranes according to embodiments of the invention are typically disposed in a housing comprising at least one inlet and at least one outlet and defining at least one fluid flow path between the inlet and the outlet, wherein at least one inventive membrane or a filter including at least one inventive membrane is across the fluid flow path, to provide a filter device or filter module. In an embodiment, a filter device is provided comprising a housing comprising an inlet and a first outlet, and defining a first fluid flow path between the inlet and the first outlet; and at least one inventive membrane or a filter comprising at least one inventive membrane, the inventive membrane or filter comprising at least one inventive membrane being disposed in the housing across the first fluid flow path.

Preferably, for crossflow applications, at least one inventive porous membrane or filter comprising at least one inventive membrane is disposed in a housing comprising at least one inlet and at least two outlets and defining at least a first fluid flow path between the inlet and the first outlet, and a second fluid flow path between the inlet and the second outlet, wherein the inventive membrane or filter comprising at least one inventive membrane is across the first fluid flow path, to provide a filter device or filter module. In an illustrative embodiment, the filter device comprises a crossflow filter module, the housing comprising an inlet, a first outlet comprising a concentrate outlet, and a second outlet comprising a permeate outlet, and defining a first fluid flow path between the inlet and the first outlet, and a second fluid flow path between the inlet and the second outlet, wherein at least one inventive membrane or filter comprising at least one inventive membrane is disposed across the first fluid flow path.

The filter device or module may be sterilizable. Any housing of suitable shape and providing an inlet and one or more outlets may be employed.

The housing can be fabricated from any suitable rigid impervious material, including any impervious thermoplastic material, which is compatible with the fluid being processed. For example, the housing can be fabricated from a metal, such as stainless steel, or from a polymer, e.g., transparent or translucent polymer, such as an acrylic, polypropylene, polystyrene, or a polycarbonate resin.

The following examples further illustrate the invention but, of course, should not be construed as in any way limiting its scope.

Materials and Methods:

The starting material was Solvay's bis-telechelic polyethersulfone VW-10700 RP described to have the terminal phenol moiety with density of 0.187 millieq of OH per gram of resin, as determined by titration. The polymer had a Mw=21332, as determined by GPC analysis in DMAc (with PS standard). All the cited data has been provided in manufacturer's certificate of analysis. In-house analysis performed in DMF with 0.05N LiBr and PMMA as a standard gave the value of Mw=31578 and PDI=1.62.

Vinyl monomers were either vacuum distilled or passed through a column containing an inhibitor remover.

Example 1

This example illustrates a general protocol of preparing copolymer A-B-A in accordance with an embodiment.

VW-10700 RP was dissolved in anhydrous NMP, followed by addition of the vinyl monomer and AIBN as radical initiator. The resulting mixture was purged with argon at ambient temperature for at least 2-5 min, followed by the heating at 80° C. for 16-24 h. After that time the reaction mixture was opened to air and added to excess of vigorously stirred non-solvent, usually at least 10 volumes of 2-propanol. The resulting precipitate was filtered-off (or centrifuged in some cases), rinsed well with 2-propanol and dried in vacuum oven at 70° C. overnight. The obtained material was analyzed by GPC (DMF with 0.05N LiBr, calibrated with PMMA molecular weight standards) and the composition was determined by $^1$H NMR analysis (in DMSO-$d_6$) and elemental analysis.

Example 2

This example illustrates a method of preparing PVP-b-PES-b-PVP, with $(m_1+m_2)/n=0.35$, in accordance with an embodiment of the invention:

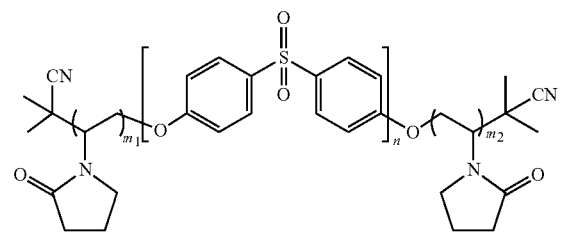

VW-10700RP (0.5 g; 0.093 mmol of OH), 1-vinylpyrrolid-2-one (1.0 mL; 9 mmol) and AIBN (8 mg; 0.047 mmol) were dissolved in anhydrous NMP (3 mL) and copolymerized according to the general protocol, yielding 0.39 g of product.

$^1$H NMR analysis indicated 35 molar % of VP unit as determined by comparing integration of signals between 7.80-8.20 ppm (4H of PES unit) and between 1.20-2.40 ppm (6H of VP unit). Elemental analysis (% N=2.46; % S=10.71) indicated 34 molar % of VP unit. GPC: Mw=31370; PDI=1.55.

Example 3

This example illustrates a method of preparing PVP-b-PES-b-PVP, with $(m_1+m_2)/n=0.50$, in accordance with an embodiment of the invention.

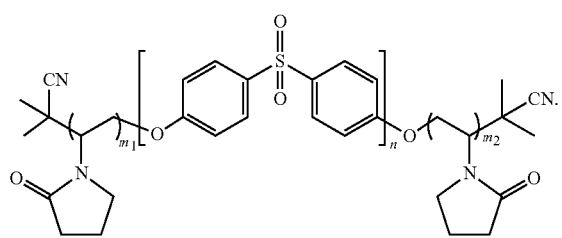

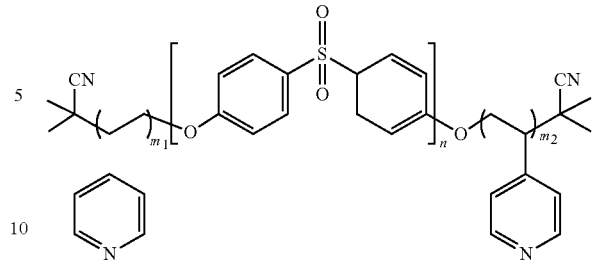

VW-10700RP (0.5 g; 0.093 mmol of OH), 1-vinylpyr-rolid-2-one (2.0 mL; 18 mmol) and AIBN (16 mg; 0.094 mmol) were dissolved in anhydrous NMP (2 mL) and copolymerized according to the general protocol, yielding 0.66 g of product.

$^1$H NMR analysis indicated 50 molar % of VP unit as determined by comparing integration of signals between 7.80-8.20 ppm (4H of PES unit) and between 1.20-2.40 ppm (6H of VP unit). Elemental analysis (% N=4.09; % S=8.56) indicated 52 molar % of VP unit. GPC: Mw=32600; PDI=1.58.

Example 4

This example illustrates a method of preparing PVAc-b-PES-b-PVAc with $(m_1+m_2)/n=0.16$, in accordance with an embodiment of the invention:

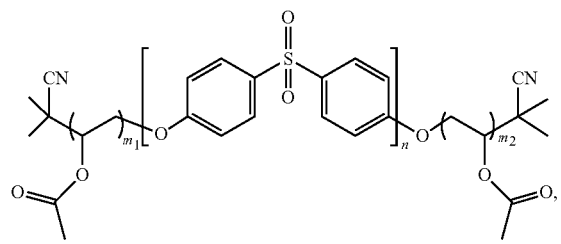

VW-10700RP (0.5 g; 0.093 mmol of OH), vinyl acetate (1.75 mL; 18.7 mmol) and AIBN (15 mg; 0.092 mmol) were dissolved in anhydrous NMP (3 mL) and copolymerized according to the general protocol, except that methanol was used as a non-solvent to precipitate and wash the product (0.57 g).

$^1$H NMR analysis indicated 16 molar % of VAc unit as determined by comparing integration of signals between 7.80-8.20 ppm (4H of PES unit) and between 4.60-4.80 ppm (1H of VAc unit). GPC: Mw=30225; PDI=1.59.

Example 5

This example illustrates a method of preparing P4VP-b-PES-b-P4VP with $(m_1+m_2)/n=0.11$ in accordance with an embodiment of the invention:

VW-10700RP (0.5 g; 0.093 mmol of OH), 4-vinylpyridine (1.1 mL; 10.2 mmol) and AIBN (15 mg; 0.092 mmol) were dissolved in anhydrous NMP (3 mL) and copolymerized according to the general protocol, using methanol as a non-solvent, yielding 0.41 g of product.

$^1$H NMR analysis indicated 11 molar % of 4-VP unit as determined by comparing integration of signals between 7.20-7.30 ppm (4H of PES unit) and between 6.50-6.70 ppm (2H of 4-VP unit). Elemental analysis (% N=1.11; % S=12.90) indicated 16 molar % of 4-VP unit. GPC: Mw=32080; PDI=1.60.

Example 6

This example illustrates a method of preparing self-wetting membrane in accordance with an embodiment of invention.

5 g of a polymer solution containing 30 wt % of PES E6020, 65 wt % of DMF and 5 wt % of NMP was combined with 12.5 g of 160 nm Li-doped HMDS-treated silica particles (described elsewhere by Harton et al.) suspended in DMF at 40 wt %. To this mixture, PEG1000 (0.23 g), PVP-K90 (0.06 g) and PVP-b-PES-b-PVP described in Example 3 (0.12 g) were sequentially added, followed by homogenization at 30,000 rpm for 5 min and degassing at 200 mbar for 30 min. The resulting mixture was cast on a preformed PVOH thin film (prepared on a glass plate from 10% stock solution dried at 80° C. for 2 h) using a drawdown casting bar, placed in an oven for 8 min at 60° C., then immediately placed in a water bath at 80° C. for 1 h. Finally, the film was soaked in 1N HCl for 30 min, washed with water, and soaked in 10% aq. KOH overnight. The resulting membrane was washed with water for 2 h and then dried at 70° C. for 1 h.

For comparison, a membrane with formulation containing WE3 (Ashland's Plasdone™ S-630 copovidone) in place of copolymer of invention, was prepared as a standard. Samples were compared in terms of wettability, water flux, particle retention and BSA solution flux and throughput. The results are presented in Table 1.

TABLE 1

Properties of Membranes

Figure 2:
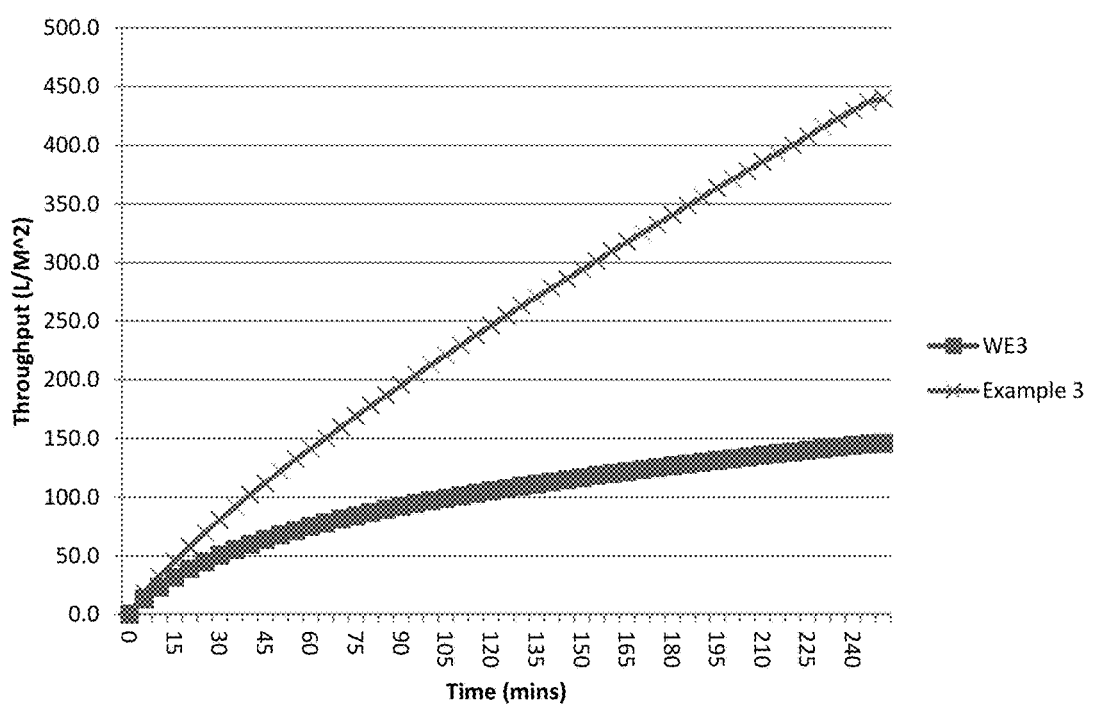
FIG. 2 depicts the BSA throughput as a function of time for the membranes depicted in FIG. 1.

| Wetting Agent | CWST (dynes/cm) | WF @10 psi (LMH) | WF @ 30 psi (LMH) | LRV (62 nm) | BSA Challenge |
|---|---|---|---|---|---|
| WE3 (PVP-co-VAc) | 69 | 482 | 368 | 2.8 | See FIG. 1 and 2 |

TABLE 1-continued

Properties of Membranes

| | Wetting Agent | | | | |
|---|---|---|---|---|---|
| | CWST (dynes/cm) | WF @10 psi (LMH) | WF @ 30 psi (LMH) | LRV (62 nm) | BSA Challenge |
| Example 3 (PVP-b-PES-b-PVP) | 71 | 615 | 418 | >3 | See FIG. 1 and 2 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A self-wetting porous membrane comprising an aromatic hydrophobic polymer and a wetting agent comprising a copolymer of formula A-B or A-B-A, wherein A is a hydrophilic segment comprising a polymerized monomer or mixture of monomers, wherein the monomer is of the formula (I):

$$CH_2=C(R^1)(R^2) \quad (I),$$

wherein $R^1$ is hydrogen or alkyl, and $R^2$ is selected from pyrrolidinonyl, imidazolyl, N-methylimidazolyl, formylamino, formylaminoalkyl, alkylcarbonyloxy, and aminocarbonylalkyl substituted with a zwitterionic group, and B is polyethersulfone, wherein segments B and A are linked through an oxygen atom;

wherein the copolymer has an end group selected from 2-methylpropionitrile, benzoate, laurate, t-butyloxy, and cumyloxy.

2. The self-wetting porous membrane of claim 1, wherein $R^1$ is hydrogen or methyl, and $R^2$ is selected from pyrrolidinonyl, imidazolyl, N-methylimidazolyl, formylamino, formylaminomethyl, methylcarbonyloxy, and aminocarbonylpropyl substituted with a zwitterionic group.

3. The self-wetting porous membrane of claim 1, wherein the monomer of A is selected from 1-vinylpyrrolid-2-one, N-[3-(dimethylamino)propyl]methacrylamide, vinyl acetate, 1-vinylimidazole, 1-vinyl-3-methylimidazole, N-vinylformamide, N-allylformamide, and 3-(methacrylamidopropyl)dimethyl(3-sulfopropyl)ammonium inner salt.

4. The self-wetting porous membrane of claim 1, wherein the aromatic hydrophobic polymer is selected from polysulfone, polyethersulfone, polyphenylene ether, polyphenylene ether sulfone, polyphenylene oxide, polycarbonate, poly (phthalazinone ether sulfone ketone), polyether ketone, polyether ether ketone, polyether ketone ketone, polyimide, polyetherimide, and polyamide-imide.

5. The self-wetting porous membrane of claim 1, wherein the aromatic hydrophobic polymer is polysulfone or polyethersulfone.

6. The self-wetting porous membrane of claim 1, wherein the wetting agent is a copolymer of the formula A-B-A and is represented by formula (Ia):

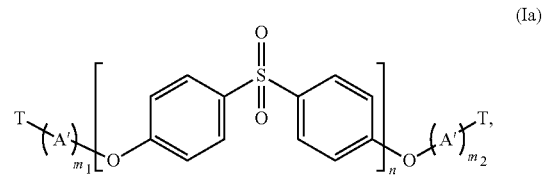

or the wetting agent is a copolymer of the formula A-B and is represented by formula (Ib):

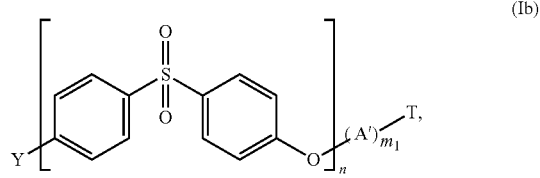

wherein A' is a polymeric segment of the hydrophilic monomer, T is an end group selected from 2-methylpropionitrile, benzoate, laurate, t-butyloxy, and cumyloxy, Y is chloro or fluoro, $m_1$ or $m_2$ is from about 5 to about 80, and n is from about 20 to about 200.

7. The self-wetting porous membrane of claim 1, wherein the copolymer is of the formula:

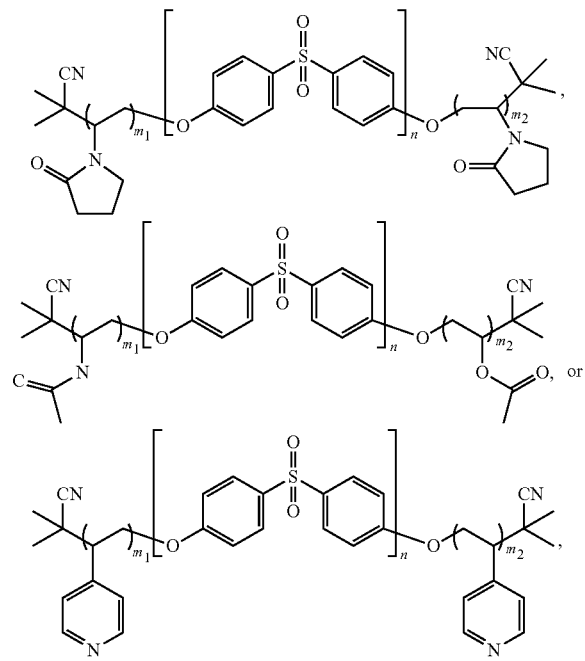

wherein $m_1$ or $m_2$ is from about 5 to about 80 and n is from about 20 to about 200.

8. A method of preparing a self-wetting porous membrane comprising:
(i) casting a solution comprising a solvent, an aromatic hydrophobic polymer, and a copolymer of formula A-B or A-B-A, wherein A is a hydrophilic segment comprising a polymerized monomer or mixture of monomers, wherein the monomer is of the formula (I):

$$CH_2=C(R^1)(R^2) \qquad (I),$$

wherein $R^1$ is hydrogen or alkyl, and $R^2$ is selected from pyrrolidinonyl, imidazolyl, N-methylimidazolyl, formylamino, formylaminoalkyl, alkylcarbonyloxy, and aminocarbonylalkyl substituted with a zwitterionic group, and
wherein the copolymer has an end group selected from 2-methylpropionitrile, benzoate, laurate, t-butyloxy, and cumyloxy,
and B is polyethersulfone, wherein segments B and A are linked through an oxygen atom, to a desired shape;
(ii) subjecting the cast solution to phase inversion to form the self-wetting porous membrane; and
(iii) optionally rinsing the self-wetting porous membrane with water.

9. The method of claim 8, wherein $R^1$ is hydrogen or methyl, and $R^2$ is selected from pyrrolidinonyl, imidazolyl, N-methylimidazolyl, formylamino, formylaminomethyl, methylcarbonyloxy, and aminocarbonylpropyl substituted with a zwitterionic group.

10. The method of claim 8, wherein the monomer of A is selected from 1-vinylpyrrolid-2-one, N-[3-(dimethylamino)propyl]methacrylamide, vinyl acetate, 1-vinylimidazole, 1-vinyl-3-methylimidazole, N-vinylformamide, and N-allylformamide, and 3-(methacrylamidopropyl)dimethyl(3-sulfopropyl)ammonium inner salt.

11. The method of claim 8, wherein the aromatic hydrophobic polymeric segment B is polyethersulfone.

12. The method of claim 8, wherein the aromatic hydrophobic polymer is selected from polysulfone, polyethersulfone, polyphenylene ether, polyphenylene ether sulfone, polyphenylene oxide, polycarbonate, poly(phthalazinone ether sulfone ketone), polyether ketone, polyether ether ketone, polyether ketone ketone, polyimide, polyetherimide, and polyamide-imide.

13. The method of claim 8, wherein the aromatic hydrophobic polymer is polysulfone or polyethersulfone.

14. The method of claim 8, wherein the copolymer of formula A-B-A is of the formula (Ia):

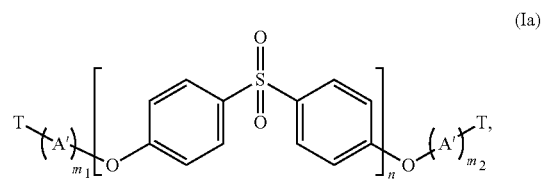

and the copolymer of formula A-B is of the formula (Ib):

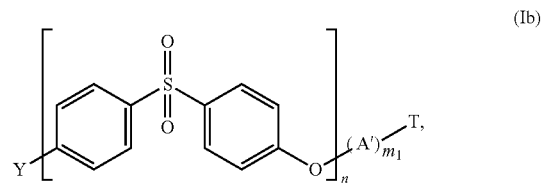

wherein A' is a polymeric segment of the hydrophilic monomer, T is an end group selected from 2-methylpropionitrile, benzoate, laurate, t-butyloxy, and cumyloxy, Y is chloro or fluoro, $m_1$ or $m_2$ is from about 5 to about 80, and n is from about 20 to about 200.

15. The method of claim 8, wherein the copolymer is of the formula:

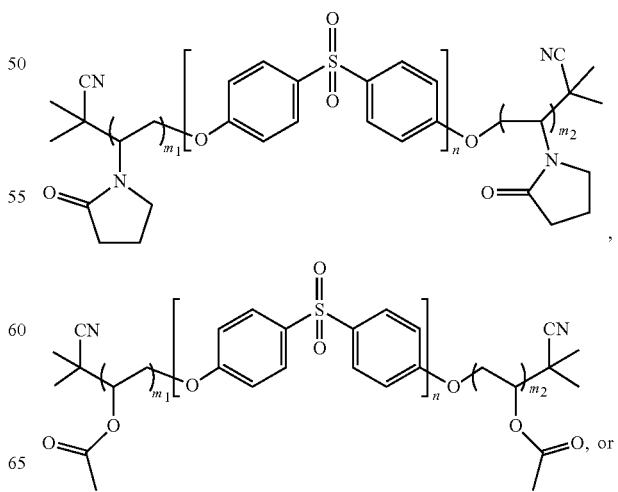

-continued
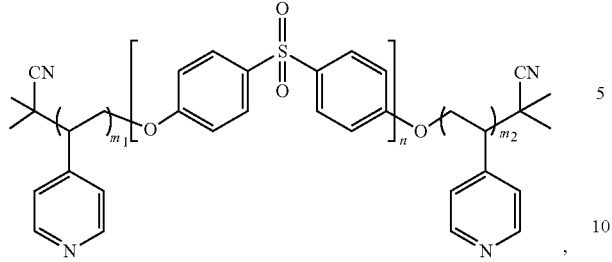
wherein $m_1$ or $m_2$ is from about 5 to about 80 and n is from about 20 to about 200.
16. A self-wetting porous membrane prepared by the method of claim 8.
17. A method of filtering a fluid, the method comprising passing the fluid through the self-wetting porous membrane of claim 1.
* * * * *